US010004446B2

(12) United States Patent
Osorio (10) Patent No.: US 10,004,446 B2
(45) Date of Patent: Jun. 26, 2018

(54) PARAMETRIC SEIZURE DETECTION (71) Applicant: Flint Hills Scientific, L.L.C., Lawrence, KS (US)

(72) Inventor: Ivan Osorio, Leawood, KS (US)

(*) Notice: Subject to any disclaimer, the term of this patent is extended or adjusted under 35 U.S.C. 154(b) by 622 days.

(21) Appl. No.: 14/170,389

(22) Filed: Jan. 31, 2014

(65) Prior Publication Data

US 2014/0276128 A1  Sep. 18, 2014

Related U.S. Application Data (63) Continuation-in-part of application No. 14/084,513, filed on Nov. 19, 2013.

(60) Provisional application No. 61/785,429, filed on Mar. 14, 2013, provisional application No. 61/793,292, filed on Mar. 15, 2013, provisional application No. 61/794,540, filed on Mar. 15, 2013, provisional application No. 61/801,950, filed on Mar. 15, 2013.

(51) Int. Cl.
*A61B 5/02* (2006.01)
*A61B 5/00* (2006.01)
*A61B 5/0205* (2006.01)
*A61B 5/024* (2006.01)

(52) U.S. Cl.
CPC ............ *A61B 5/4094* (2013.01); *A61B 5/024* (2013.01); *A61B 5/0205* (2013.01)

(58) Field of Classification Search
CPC ...... A61B 5/4094; A61B 5/024; A61B 5/0205
See application file for complete search history.

(56) References Cited

U.S. PATENT DOCUMENTS

| | | | |
|---|---|---|---|
| 2010/0121215 A1* | 5/2010 | Giftakis | A61B 5/031 600/544 |
| 2012/0277605 A1* | 11/2012 | Colborn | A61B 5/024 600/508 |

* cited by examiner

*Primary Examiner* — Tiffany Weston
(74) *Attorney, Agent, or Firm* — CF3; Stephen Eisenmann (57) ABSTRACT

We report a method for detecting epileptic or non-epileptic seizures, comprising: receiving a heart rate of a patient; calculating a percentage change of the heart rate in reference to at least one of the patient's maximal heart rate, reserve heart rate, or a resting heart rate; detecting an epileptic seizure if the percentage increase in the heart rate reaches a threshold value; and taking at least one responsive action selected from issuing a warning, delivering a therapy, determining a seizure severity, or logging at least one of a date and time of occurrence of the seizure, its severity, the type of therapy, or its effect, in response to the detection. We also report a medical device system configured to implement the method. We also report a non-transitory computer readable program storage unit encoded with instructions that, when executed by a computer, perform the method.

8 Claims, 6 Drawing Sheets

PARAMETRIC SEIZURE DETECTION

CROSS-REFERENCE TO RELATED APPLICATIONS

This application claims priority to prior U.S. provisional patent applications 61/785,429, filed Mar. 14, 2013; and 61/793,292, 61/794,540, and 61/801,950, all filed Mar. 15, 2013, and is a continuation-in-part of U.S. patent application Ser. No. 14/084,513, filed Nov. 19, 2013, which are hereby incorporated by reference.

FIELD OF THE INVENTION

This disclosure relates to medical device systems and methods capable of detecting epileptic seizures.

SUMMARY OF THE INVENTION

In some embodiments, the present disclosure relates to a method for detecting an epileptic seizure, comprising: receiving a heart rate of a patient; calculating a percentage change of the heart rate in reference to at least one of the patient's maximal heart rate, a reserve heart rate, an activity heart rate, or a resting heart rate; detecting an epileptic seizure if the percentage increase in the heart rate reaches a threshold value; and taking at least one responsive action selected from issuing a warning, delivering a therapy, determining a seizure severity, or logging at least one of a date and time of occurrence of the seizure, its severity, the type of therapy, or its effect, in response to the detection. Other cardiac signals, such as myocardial contractility, ejection fraction, etc., may be applied for detection of brain state changes such as epileptic seizures.

In other embodiments, the present disclosure relates to a medical device system, comprising one or more components configured to implement part or all of one or more of the steps of the method.

In some embodiments, the present disclosure relates to a non-transitory computer readable program storage unit encoded with instructions that, when executed by a computer, perform a method as described above.

BRIEF DESCRIPTION OF THE DRAWINGS

The disclosure may be understood by reference to the following description taken in conjunction with the accompanying drawings, in which like reference numerals identify like elements, and in which.

While the disclosure is susceptible to various modifications and alternative forms, specific embodiments thereof have been shown by way of example in the drawings and are herein described in detail. It should be understood, however, that the description herein of specific embodiments is not intended to limit the disclosure to the particular forms disclosed, but on the contrary, the intention is to cover all modifications, equivalents, and alternatives falling within the spirit and scope of the disclosure as defined by the appended claims.

DETAILED DESCRIPTION OF SPECIFIC EMBODIMENTS

Illustrative embodiments of the disclosure are described herein. For clarity, not all features of an actual implementation are described. In the development of any actual embodiment, numerous implementation-specific decisions must be made to achieve design-specific goals, which will vary from one implementation to another. Such a development effort, while possibly complex and time-consuming, would nevertheless be a routine undertaking for persons of ordinary skill in the art having the benefit of this disclosure.

More information regarding detecting an epileptic event from cardiac data, as well as information regarding measures of central tendency that can be determined from time series of body data, may be found in other patent applications assigned to Flint Hills Scientific, LLC or Cyberonics, Inc., such as, U.S. Ser. No. 12/770,562, filed Apr. 29, 2010; U.S. Ser. No. 12/771,727, filed Apr. 30, 2010; U.S. Ser. No. 12/771,783, filed Apr. 30, 2010; U.S. Ser. No. 12/884,051, filed Sep. 16, 2010; U.S. Ser. No. 13/554,367, filed Jul. 20, 2012; U.S. Ser. No. 13/554,694, filed Jul. 20, 2012; U.S. Ser. No. 13/559,116, filed Jul. 26, 2012; and U.S. Ser. No. 13/598,339, filed Aug. 29, 2012. Each of the patent applications identified in this paragraph is hereby incorporated herein by reference.

More information regarding detecting an epileptic event from multiple body data types, and examples of such body data types, may be found in other patent applications assigned to Flint Hills Scientific, LLC or Cyberonics, Inc., such as, U.S. Ser. No. 12/896,525, filed Oct. 1, 2010, now U.S. Pat. No. 8,337,404, issued Dec. 25, 2012; U.S. Ser. No. 13/098,262, filed Apr. 29, 2011; U.S. Ser. No. 13/288,886, filed Nov. 3, 2011; U.S. Ser. No. 13/554,367, filed Jul. 20, 2012; U.S. Ser. No. 13/554,694, filed Jul. 20, 2012; U.S. Ser. No. 13/559,116, filed Jul. 26, 2012; and U.S. Ser. No. 13/598,339, filed Aug. 29, 2012. Each of the patent applications identified in this paragraph is hereby incorporated herein by reference.

Embodiments of the present disclosure provide for determining a patient's maximal heart rate (MHR), a resting heart rate (RSR), a reserve heart rate (RvHR), an activity heart rate (AHR) and a activity reserve heart rate (ARvHR), for use as a reference to detect changes in brain or body state. The patient's heart rate may be monitored and a change in the heart rate may be detected and measured. If a heart rate change occurs, the heart rate upon which a detection may be attempted, may be analyzed relative to the at least one of the references MHR, RSR, RvHR, AHR, or ARvHR. If the percentage change of the patient's heart rate, in reference to at least one of the MHR, RSR, RvHR, AHR, or ARvHR is above a threshold change (or in certain cases below it) then an epileptic seizure is deemed to have been detected. Sub-reference heart rate values such as resting heart rate awake (RSRw), heart rate asleep (RSRs) and for sleep, heart rate asleep REM (RSRsrem), heart rate asleep Non-REM (RSRsnrem), reserve heart rate awake (RvHRw) or reserve heart rate asleep (RvHRs), etc., may be used to improve accuracy and speed of detection of epileptic seizures and other brain or body state changes.

The magnitude and direction (e.g., increases or decreases) of heart changes associated with epileptic seizures vary as a function of extent of involvement of the brain by paroxysmal activity (which is generally partially a function of time) and of certain anatomo-functional factors such as location of the epileptogenic network. The location of the epileptogenic network location may have a positive or negative chronotropic effect of variable magnitude. Therefore, ictal heart rate changes may manifest as increases or decreases in the same patient and may be small or large. Upon detecting an epileptic seizure, a response action may be taken, wherein the responsive action may include issuing a warning, delivering a therapy, determining a seizure severity, or logging at least one of a data and time of the seizure, its severity, the type of therapy or its effect.

The value (e.g., amplitude, frequency, concentration, rate of change, etc.) of biological (e.g., autonomic, endocrine, metabolic, neurological, etc.) signals from a patient may change as function of one or more of the state of the patient's health, physical or cognitive activity type and levels of the patient, the patient's fitness level, time of day, or the patient's level of consciousness. The state dependency and associated fluctuations (physiological or pathological) of these signals complicates the detection of events, and especially their accurate classification into physiological/desirable or pathological/undesirable. For example, epileptic seizures may increase the heart rate from 80 bpm to 120 bpm, but a similar change may be caused by exercise, emotions, or certain diseases. While resorting to multimodal signals (e.g., heart rate, rate of heart change, EKG morphology, measurement of movement using accelerometers) may in the example above sort out exertional from epileptic increases in heart rate, a more economical and simpler approach is disclosed herein to classify or identify changes in biological signals as either desirable or undesirable, and based on their type, take responsive action that protects the patient's health and well-being. This approach uses certain references (e.g., RSR, MHR, RvHR, etc.) that in the absence of cardiac disease, generally do not change or may change very slowly and/or by very small quantities, behaving as parameters in a dynamical sense, a characteristic that makes them useful as references for detection of state changes given their high stationarity. The behavior of these parameters is fairly stable, unlike the behavior of variables such as instantaneous heart rate (IHR) and instantaneous respiratory rate, catecholamines levels, etc., that change rapidly and also markedly in response to exercise, emotions, cognitive activity or metabolic and endocrine factors, which may change rapidly.

As used herein, a biological signal, such as heart rate, may be a variable (e.g., instantaneous heart rate subject to rapid (e.g., <<1 sec) and large (e.g., 80 bpm) variations) or a parameter (e.g., maximal heart rate that does not change or changes very slowly in the absence of cardiac disease).

The range of fluctuation of autonomic, neurological, endocrine, metabolic, and tissue stress signals are bounded, reaching absolute maximum (global maximum) or minimum (global minimum) values. For example, there is a maximal heart rate defined by the formula 220−age, as well a resting heart rate that remains relatively constant with age. While the different classes of signals listed above have global maxima and global minima, and may be used for detection of undesirable state changes, it may be desirable to use heart rate due to its ease of acquisition/recording, its high signal to noise ratio (relative to many other biological signals), and its ease of computation.

Factors such as age, fitness level, body weight, maximal heart rate, resting heart rate during wakefulness, heart rate during sleep, environmental conditions (conditions external to the patient's body, e.g., temperature, humidity, altitude), etc., are generally not taken into account for setting thresholds for automated detection of pathological events in biological time series that are inherently non-stationary. For example, state-of-the art automated algorithms for epileptic seizure detection based on heart rate do not take into account these parameters, relaying chiefly if not exclusively on variables such as changes in instantaneous heart rate. As a result, inherent and ubiquitous non-ictal fluctuations in those signals are likely to result in false positive or false negative detections using prior techniques.

Seizure detection performance may be improved in a highly computationally efficient manner by using as reference values a patient's one or more parameters and/or normalized values. Examples of such reference values include:

1. Maximal heart rate (MHR)—HR which may be calculated using the formula 220−patient's age or any other valid formula;
2. Resting heart rate (RHR)—HR as measured during sedentary active wakefulness or during sleep;
3. Reserve heart rate (RvHR)—HR which may be calculated as the difference between the maximal heart rate and the resting heart rate [e.g., RvHR=MHR (220 bpm−40 years old)−RHR (60 bpm)=120 bpm]; or,
4. Activity reserve heart rate (ARvHR)—HR which may be calculated as the difference between the MHR and the current measured heart rate (CMHR), which will depend on a current activity level or work level (i.e., a physiological increase in HR).

"Work level" herein refers to the energy consumption of the patient's body or a part thereof (e.g., the brain). Energy consumption may, in some embodiments, be measured by differences in oxygen saturation, concentration, or pressure between arterial and venous locations. In some embodiments of this disclosure, work level may be determined using measures of kinetic activity (force, amplitude, velocity, direction, and duration and rate of muscle contractions) or autonomic activity such as heart rate. "Work level" in this disclosure does not refer exclusively to the patient's physical activity. Physical activity may be only one of multiple physiological events or states leading to energy consumption by the patient's body or a part thereof. "Work level" may also refer to the physics definition, $W=F \times d$. The application of force over distance may be only one of multiple actions by a patient leading to energy consumption by the patient's body or a part thereof.

Each of these reference values may be further refined to capture different aspects of a patient's body state (e.g., resting heart rate during non-rapid eye movement (NREM) sleep, Resting heart rate during REM sleep). Further, the HR rate associated with the current activity or work level may vary based upon the level of exertion associated with the current activity or work level (i.e., a patient's HR is likely to be higher while jogging than while walking).

The HR resulting from current activity or work level may be physiological/normal (e.g., exercise) or pathological/abnormal (e.g., epileptic seizure). Current measured signal value (CMSV) is defined herein generally as the signal value being analyzed to determine whether the patient has undergone a change, and whether the change was a result of physiological or pathological activity. In one embodiment a current (i.e., present time) measured signal value (CMSV) may comprise an instantaneous value, a median or mean value of a short term time window (e.g., less than thirty seconds). Current measured heart rate (CMHR) is a currently measured signal value resulting from measurement of a signal value relative to the heart.

In yet other embodiments, autonomic activity (e.g., respiration, catecholamines), neurologic activity (e.g., kinetic activity that includes force of contraction), endocrine activity (e.g., cortisol), metabolic activity (e.g., oxygen consumption) may be used instead of or along with cardiac activity. In other words, autonomic (e.g., $SaO_2$), metabolic (arterial pH, lactic acid production and clearance, oxygen consumption), neurologic (e.g., frequency, velocity, force of muscle contractions, number of body parts involved), tissue stress factors, etc., may be used in a manner similar to cardiac signals. For example, minimal and maximal oxygen consumption, reserve oxygen consumption (the difference between maximal and current consumption whether during resting conditions or while engaged in physical activity) may be used for detection of certain seizures. Under certain conditions, the reference values of parameters may be pathological but changes in said values may be used for detection of state changes. Any of the body signals or indices (e.g., respirations, body movements, etc.) may be used to validate and verify detection performance based on another body signal. For example, detections using heart rate may be validated using body movements (e.g., kinetic signals). False positive or false negative detections may be identified by comparing changes in a body signal value with a different body signal, to improve detection performance and clinical usefulness.

Ratios or other mathematical expressions between these parameters/variables may be used instead of their differences.

One of the advantages of the approach disclosed herein compared to the present state of the art that requires the continual collection and calculation of a foreground and background value. By way of an example of a present state of the art methodology, HR is used to compute a foreground/background value that is then analyzed relative to various detection thresholds. In contrast, in the present approach, continual background/foreground updating is unnecessary since MHR, RHR are known and highly stable. Typically MHR and RHR change by no more than 1 bpm/year under normal circumstances. Another noteworthy advantage to the present approach is the data normalization inherent to this approach for a patient's physiological traits (e.g., the patient's age, fitness level and current heart or respiratory rate values). While only heart and respiratory signals have been mentioned herein, other autonomic, endocrine, neurologic, metabolic or body stress marker signals may be applied for seizure detection.

EXAMPLE 1

Patient is 40 years old. MHR=180 bpm; RHR 60 bpm; RvHR: 120 bpm. An event is occurring that increases the patient's heart rate to a current measured value (CMHR) of 155 bpm. If a seizure occurs when this patient is resting, the large difference between the RHR and the CMHR (e.g., Current measured value (CMHR)(155 bpm)−RHR (60 bpm)=+95 bpm) strongly suggests that the change in heart rate is indicative of a seizure, and that the probability of a false positive or false negative detection is low. However, if the patient was exercising instead of resting just prior to the time of seizure onset, with a prior measured heart rate (PMHR) at 140 bpm, (corresponding to an ARvHR of 40 bpm), the detection margin is a much smaller +15 bpm (e.g., Current measured value (155 bpm)−PMHR (140 bpm)=+15 bpm), and the smallness of this margin increases the probability of a false negative detection unless some adaptation is made. However such an adaptation (e.g., reduction of the detection threshold) would increase the probability of a false positive detections at other times/circumstances unless the adaptation were "intelligent" since sensitivity and specificity of detection compete with each other (i.e., one of these variables cannot be optimized without degrading the other).

One of the most commonly used event detection strategies is to parse the data into two segments, one containing the most contemporaneous data (e.g., foreground) and the other, older data that serves as reference (e.g., background) against which changes in the foreground are determined. The choice of certain parameters such as length of the background/reference segment and the rate at which it is updated, is made to reduce its innate variability and minimize the negative impact it may have on the performance (sensitivity specificity and speed of event detection) of the detection algorithm. The steps taken to reduce potentially large fluctuations in the value(s) of the reference/background segment, are only partially successful in minimizing detection performance "glitches" since the degree of reduction in non-stationarity/variability that would be required to reduce the task of event detection from a "two-variable problem" (that loosely speaking may be labeled as "pseudo-intractable") to a one-variable (tractable) problem will markedly degrade its information (dynamical) content to the detriment of detection performance. This invention makes the detection problem highly tractable (while optimizing detection performance) by selecting reference values (e.g., MHR, RHR) that while highly representative/informative of the dynamics of the system under study, are not subject to wide or rapid fluctuations, thus behaving as parameters in a dynamical sense. In short, this invention reduces a "2-variable" problem into a 1-variable without sacrificing dynamical information. The 2-variable event detection problem posed by the foreground/background approach in non-stationary (EEG, EKG) time-series is more complex than the one in algebra since the variables in the case of the time series used for seizure detection are non-stationary (i.e., continuously varying). Methodologies dependent upon foreground and background time window-based heart rates, both of which are non-stationary (the 2-variables problem) are associated with a higher probability of false positive and false negative detections than would those with only one variable (e.g., foreground).

Returning to Example 1, if the heart rate just prior to the time of seizure onset is 60 bpm (e.g., the patient is asleep), almost any threshold value (e.g., an absolute number of beats, such as +15 bpm or +30 bpm, or a percentage value, such as +25%) may be applied without adversely impacting sensitivity of detection. If speed of detection is highly important for therapeutic efficacy and to avoid injuries via early warning, low increases (e.g., +15 bpm or even a smaller (<+15 bpm) increase may serve this purpose even better. By contrast, if the heart rate just prior to the time of seizure onset is 140 bpm, leaving a detection margin of only +15 bpm, the probability of a false negative detection would increase. However, if the patient's resting heart value during wakefulness or sleep is selected as a reference value (i.e., a fiducial) the resultant increase in the detection margin (from +15 to a minimum of +70 bpm and to as much as +95 bpm) would improve detection performance under certain circumstances or conditions (where sensitivity and speed of detection are paramount for patient safety or therapeutic efficacy) by decreasing the probability of false negative detections. A previously measured heart rate (PMHR) (e.g., 140 bpm) to reference value (e.g., RHR=60 bpm) dimensionless ratio (140/60=2.3) may be also calculated. Any increases in the ratio above a threshold value (e.g., 2.3), as would be the case if the rate increased from 140 bpm to 155 bpm (155/60=2.6), would trigger a seizure detection and other actions, such as therapy delivery.

While the positive (+) sign has been used in describing these concepts, the present invention contemplates the use of routine mathematical transformations that would yield comparable results, e.g., subtracting larger positive numbers from smaller positive numbers to yield negative values having the same absolute value as the reverse subtraction, i.e., |75 bpm−60 bpm|=|60 bpm−75 bpm|, or quantifying an increase as a percentage relative to a baseline instead of an absolute number of beats per minute, among other mathematical operations known to the person of ordinary skill in the art. It should be noted that epileptic seizures may also cause bradycardia, although with a prevalence much lower than tachycardia. Regardless, the approaches (with appropriate modifications) in this disclosure may be applied to both cases.

The choice of reference value (e.g., MHR v. RHR v. RvHR v. ARvHR) upon which detections is based may depend on the state of the patient (e.g., awake v. asleep; resting v. in motion, etc.), which is correlated (in otherwise healthy epileptics) with heart rate values (i.e., low (e.g., 60-70 bpm) heart rate values indicate an adult subject is resting, intermediate values (e.g., 80-90 bpm) a moderately physically active subject and higher values (e.g., 110-140 bpm) an indicator that the subject may be jogging), by extension on the Current Measured HR, and/or the performance (false positive, false negative, positive predictive value, speed of detection, etc.) required of a detection method to maximize patient safety and therapeutic efficacy. For example, when a patient is asleep or resting, the heart rate is near its global minima, so that the probability of false seizure detections based on changes in the Current Measured heart rate (CMHR) (e.g., HR in sleep is 60 bpm (RHR) and suddenly jumps to 90 bpm, which would equal an increase of 33%) if used as the reference value, is likely to be higher compared to a detection using as a reference value the heart rate while the patient is exercising or one of the RHR or ARvHR. In this example (patient asleep with low heart rate), MHR may be the preferred reference value. However, if the patient is exercising and the CMHR is 140 just prior to the time of seizure onset, the issuance of detection will take longer than at a lower CMHR, while the probability of not detecting the seizure will also be higher (vis-à-vis a lower CMHR), especially if the heart rate change increase caused by a seizure (i.e., a pathological change equal to +15 bpm in this case) is modest; basing the detection on a percentage change of the resting heart rate (RHR) will increase the probability of detecting the seizure. In general, the lower the CMHR, the more the MHR would be the preferred reference choice, while for higher CMHR, the RHR may be the preferred reference for detection of seizures. In one embodiment, the increase in heart rate above an CMHR caused by a seizure (SzHR) may be used as the preferred reference for detection purposes and in another embodiment, the increase in heart rate caused by activity (other than seizures) above a resting value may be used as a reference value.

As used herein, when a value is said to be "near" a reference value, it may have a percentage value within, e.g., ±10% of the reference value, and/or a percentile value placing it within, e.g., the decile, the quartile, or the like of the value's distribution closest to the reference value.

The case when seizures occur during transitions from one state to another state (e.g., as from sleep to wakefulness, wakefulness to sleep physical activity to physical inactivity, or physical inactivity to physical activity) may require a different approach than the one previously outlined. Since state transitions are typically accompanied by changes in heart rate (increase or decreases), independent of those caused by epileptic seizures or other pathological events, accurate detection of undesirable events may be limited by the temporal overlap of non-epileptic and epileptic changes. One of several possible strategies to address this is to "fix" the prevailing Current Measured heart rate (CMHR) for a certain time period (e.g., 2 min) so that if seizures occur during state transition that are associated with large (or confounding for detection purposes) non-epileptic changes in heart rate, detection performance will not be degraded. The length of the window for fixation of a variable may be optimized based on historical data and optimized on- or, off-line. The process of adaptation and optimization may be iterative and encompass not only the case alluded to in this paragraph but also seizure detection within a state.

These reference values (e.g., MHR, RHR, RvHR, ARvHR may be put into various formulae or equations to determine, in a more reliable manner, which increases (or decreases) in heart rate are indicative of the occurrence of an epileptic seizures. In a particular embodiment, one or more of the reference and/or subreference values described herein may be used to partially or wholly distinguish epileptic seizures from non-epileptic seizures. More information on distinguishing epileptic seizures from non-epileptic seizures is provided in U.S. Ser. No. 13/288,886, filed Nov. 3, 2011, which is hereby incorporated herein by reference.

In one embodiment, one or more of the reference and/or subreference values described herein may be used to determine a confidence index for the sensitivity and/or specificity of detections.

Figure 1:
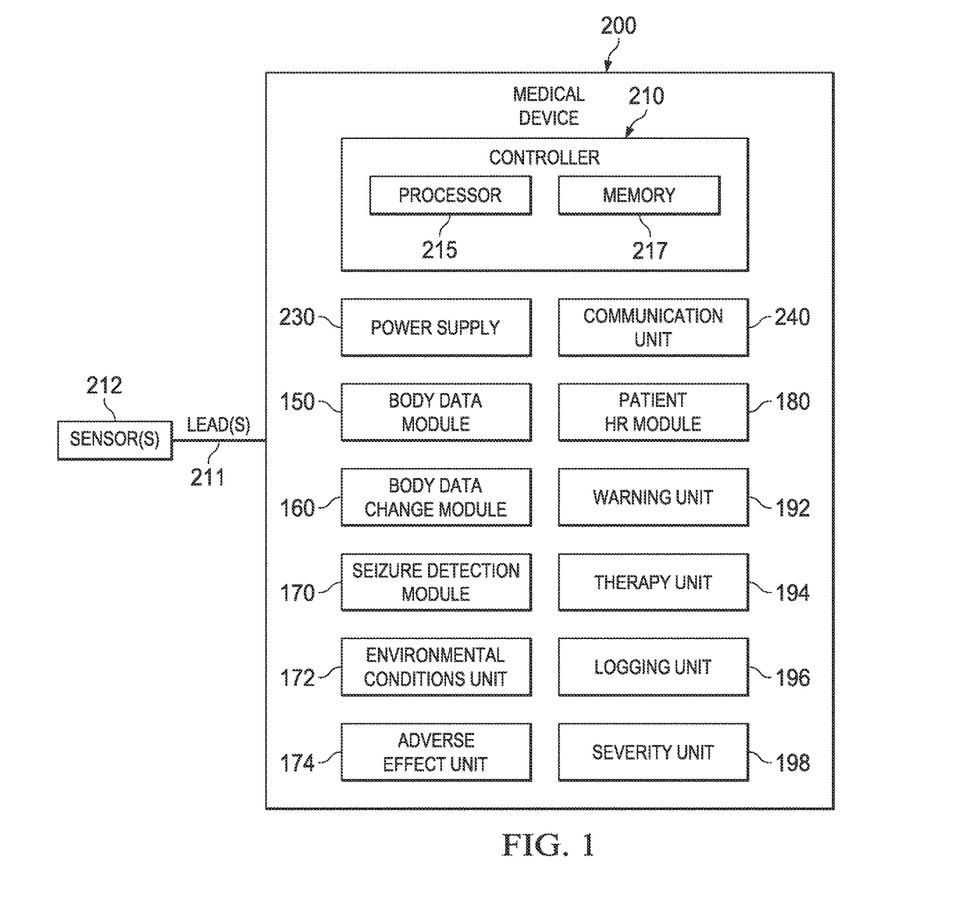
FIG. 1 shows a schematic diagram of a medical device system, according to some embodiments of the present disclosure.

FIG. 1 shows a schematic diagram of a medical device system 200, according to some embodiments of the present disclosure. The medical device system 100 may comprise a medical device 200, sensor(s) 212, and lead(s) 211 coupling the sensor(s) 212 to the medical device 200. The sensor(s) 212 may be configured to collect one or more body signals from a patient, such as autonomic, kinetic, or other body signals. In one embodiment, the at least one sensor 212 is configured to collect at least one cardiac signal.

Various components of the medical device 200, such as controller 210, processor 215, memory 217, power supply 230, communication unit 240, warning unit 192, therapy unit 194, logging unit 196, and severity unit 198 have been described in other patent applications assigned to Flint Hills Scientific, LLC or Cyberonics, Inc., such as those incorporated by reference, supra. In one embodiment, the medical device 200 may comprise a body data module 150 configured to receive a heart rate value of the patient, based at least in part on the cardiac signal, and optionally also on an environmental conditions unit 172 providing, for example, information about temperature, humidity, altitude, luminance, ambient loudness, and/or electro-magnetic noise, among others.

The medical device 200 may comprise a body data change module 160 configured to calculate a percentage change of the heart rate in reference to at least one of the patient's maximal heart rate, reserve heart rate, or a resting heart rate. Other functions, such as choosing the signal type (autonomic and/or kinetic, among others) and/or the number of signals (one or more), may be performed by medical device 200.

In some embodiments, the body data change module 160 may be configured to select the resting heart rate (RHR) from at least one of a non-REM sleep heart rate (RSRsnrem), a REM sleep heart rate (RSRsrem), an immediately upon awakening in a recumbent position resting heart rate, an immediately upon awakening in a sitting position resting heart rate, an immediately upon awakening standing still resting heart rate, a sometime after awakening standing still resting heart rate, a sometime after awakening in a recumbent position resting heart rate, a sometime after awakening in a sitting position resting heart rate, a resting heart rate after having completed a physical activity, a resting heart rate awake (RSRw), a heart rate asleep (RSRs).

In some embodiments, the body data change module 160 may be configured to determine the reserve heart rate is one of the difference between the patient's maximal heart rate and a resting heart rate, or the difference between the maximal heart rate and an activity heart rate.

The medical device 200 may comprise a patient heart rate (HR) module 180. The patient HR module 180 may be configured to provide the values of the MHR, RHR, RvHR, AHR, and the ARvHR. In one embodiment, the values of the MHR, RHR, RvHR, ARvHR, and the AHR may be stored in the patient HR module 180, wherein in other embodiments, these values may be calculated, and/or updated by the patient HR module 180.

In some embodiments, the body data change module 160 may be configured to select the maximal heart rate, the reserve heart rate, the reserve activity heart rate, the activity heart rate, or the resting heart rate based on at least one of an instantaneous heart rate value, a time of day, a state of the patient (e.g., awake v. asleep), a change in a patient health status, a change in fitness level, a change in body weight, a change in body mass index, or at least on changes in medications (with cardiovascular effects) prescribed to the patient.

Alternatively or in addition, the medical device 200 may comprise a threshold modification module (not shown). The threshold modification module may be configured to modify the threshold value based on at least one of a time of day, a state of the patient, a patient health status, at least one environmental condition, or at least one medication prescribed to the patient.

The embodiment shown in FIG. 1 shows various modules, such as body data module 150, body data change module 160, and patient HR module 180, as separate modules. In other embodiments (not shown), one or more of modules 150, 160, or 180 may be a component of another of modules 150, 160, or 180 and/or another module of medical device 200. For example, in one embodiment (not shown), patient HR module 180 may be a component of body data change module 160.

The medical device 200 may comprise a seizure detection module 170 configured to detect an epileptic seizure if the percentage increase in the heart rate reaches a threshold value.

The medical device 200 may comprise at least one additional module selected from a warning unit 192 configured to issue a warning of the seizure, a therapy unit 194 configured to deliver a therapy for the seizure, an adverse effect unit 174 configured to determine the presence of and optionally, if present, assess an adverse effect of the therapy, a severity unit 198 configured to determine a seizure severity, or a logging unit 196 configured to log at least one of a date and time of occurrence of the seizure, its severity, the type of therapy, or its effect.

Figure 2:
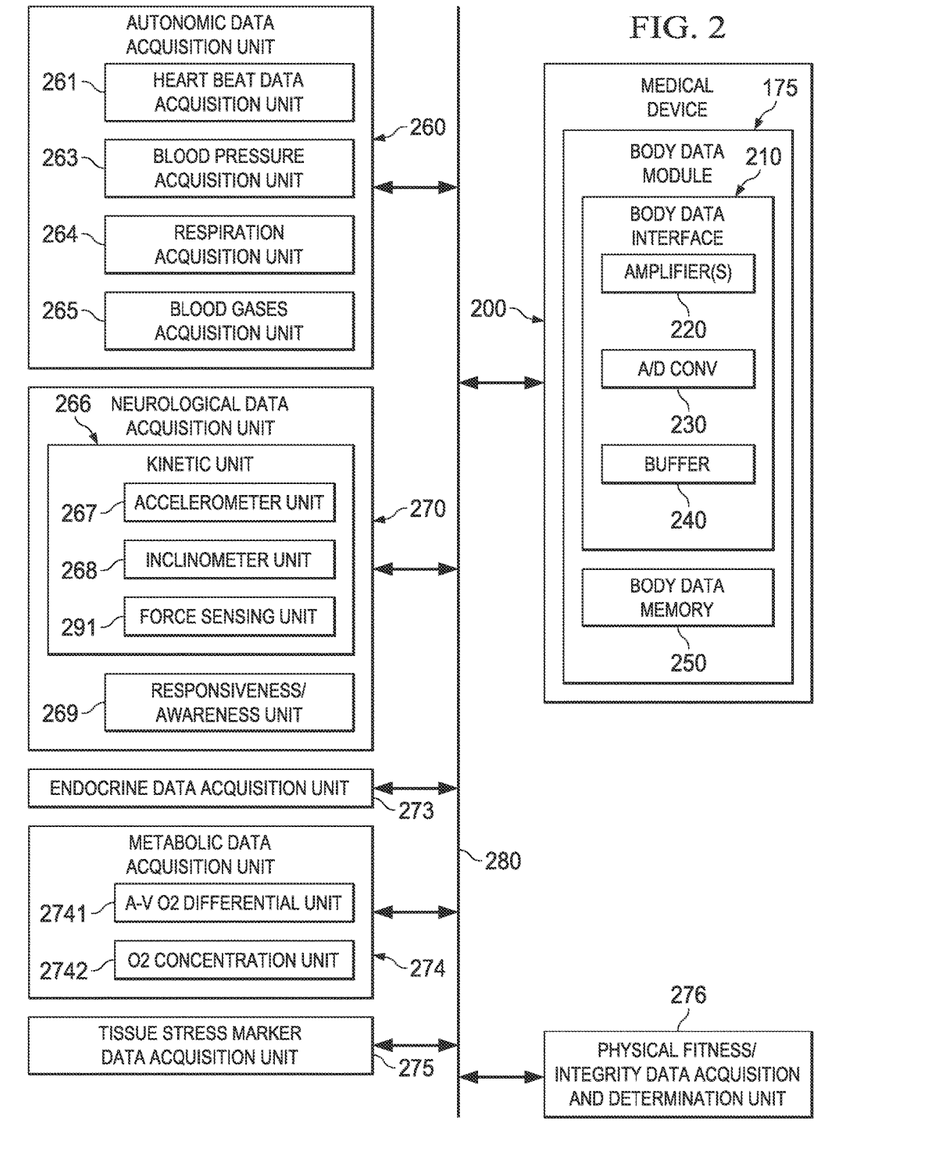
FIG. 2 shows a schematic diagram of data acquisition elements of a medical device system, according to some embodiments of the present disclosure.

FIG. 2 shows a schematic representation of components of the medical device system, particularly, body data module 150 of medical device 200, as well as an autonomic data acquisition unit 260, a neurological data acquisition unit 270, an endocrine data acquisition unit 273, a metabolic data acquisition unit 274, and a tissue stress marker data acquisition unit 275. More information regarding multiple body data types, data collection thereof, and use thereof in epileptic event detection may be found in other patent applications assigned to Flint Hills Scientific, LLC or Cyberonics, Inc., such as, U.S. Ser. No. 12/896,525, filed Oct. 1, 2010, now U.S. Pat. No. 8,337,404, issued Dec. 25, 2012; U.S. Ser. No. 13/098,262, filed Apr. 29, 2011; U.S. Ser. No. 13/288,886, filed Nov. 3, 2011; U.S. Ser. No. 13/554,367, filed Jul. 20, 2012; U.S. Ser. No. 13/554,694, filed Jul. 20, 2012; U.S. Ser. No. 13/559,116, filed Jul. 26, 2012; and U.S. Ser. No. 13/598,339, filed Aug. 29, 2012. Each of the patent applications identified in this paragraph is hereby incorporated herein by reference.

The body data module 150 may also comprise a force sensing unit 291 configured to determine an amount of force generated by part or all of a patient's body, which may provide an indication of the patient's activities.

The body data module 150 may also comprise a blood gases acquisition unit 265. In some embodiments, blood gases acquisition unit 265 may be configured to detect blood oxygen saturation at one or more points in a patient's carotid artery, jugular vein, superior vena cava, inferior vena cava, or a left ventricle of the heart. In alternative embodiments, blood gases acquisition unit 265 may be configured to detect blood oxygen saturation in additional blood vessels and/or organ target sites of the patient's body. In some embodiments, blood gases unit 265 may comprise an arterio-venous oxygen difference determination unit 2741 configured to determine an arterio-venous oxygen difference, and an oxygen consumption determination unit 2742 configured to determine an oxygen consumption from the arterio-venous oxygen difference. In yet other embodiments, $CO_2$ pressures or concentrations may be measured.

Figure 3:
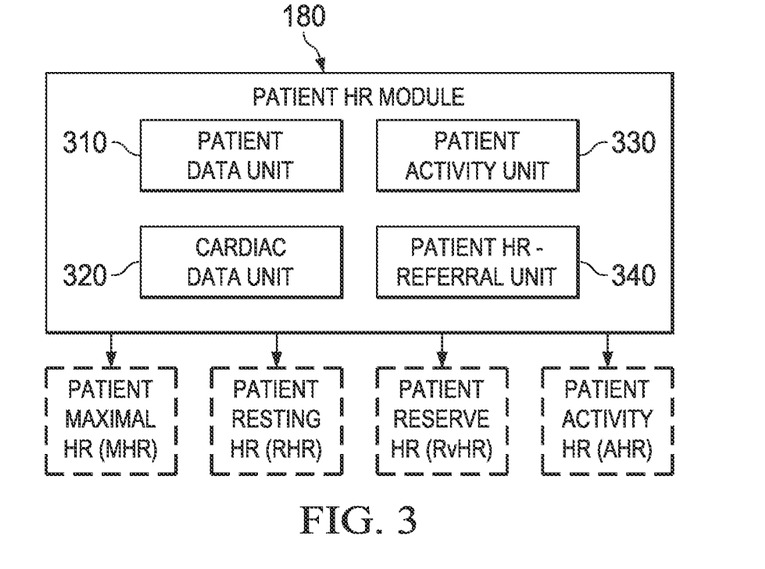
FIG. 3 shows a schematic diagram of a patient heart rate module of a medical device system, according to some embodiments of the present disclosure.

Turning now to FIG. 3, a stylized block diagram depiction of the patient HR module 180, in accordance with one embodiment, is illustrated. The patient HR module 180 comprises a patient data unit 310, a cardiac data unit 320, a patient activity unit 330, and a patient HR-reference unit 340. The patient data unit 310 may receive body data, as well as general data about the patient. For example, the patient's age, general health, fitness level, specific health issues, medication regimens, etc., may be stored in the patient data unit. These data may be used by the cardiac data unit 320 to determine relevant heart data that could impact the values of the MHR, RHR, RvHR, PMHR, and the ARvHR. Further the patient activity unit 330 may comprise data relating the patient's activity level, current activities, and/or historical activities. Data from the cardiac data unit 320 and the patient activity unit 330 may be used by the patient HR-reference unit 340 to select a parameter reference from one of MHR, RHR, RvHR, and/or the ARvHR, based on the heart rate at the time of a change in the present/current heart rate, or more specifically on the heart rate immediately prior to the onset of a seizure (CMHR). ("Present/current heart rate" encompasses, but is not limited to, an instantaneous heart rate). While emphasis has been placed on epileptic seizure detection, non-epileptic seizure detection is feasible using this invention, given the quantitative differences in changes in various body signals between epileptic and non-epileptic seizures. For example, changes in autonomic, metabolic, endocrine, neurologic, and/or tissue stress signals may be more pronounced and/or longer-lasting with epileptic than non-epileptic seizures.

In some embodiments, the present disclosure relates to a method for detecting an epileptic seizure, comprising receiving a heart rate of a patient; calculating a percentage change of the heart rate in reference to at least one of the patient's maximal heart rate (MHR), reserve heart rate (RvHR), activity reserve heart rate (ARvHR), or a resting heart rate (RHR); detecting an epileptic seizure if the percentage increase in the heart rate reaches a threshold value; and, taking at least one responsive action selected from issuing a warning, delivering a therapy, determining a seizure severity, or logging at least one of a date and time of occurrence of the seizure, its severity, the type of therapy, or its effect, in response to the detection.

The resting heart rate (RHR) may be selected from one of an NREM sleep resting heart rate, a REM sleep resting heart rate, an immediately upon awakening in a recumbent position resting heart rate; an immediately upon awakening in a sitting position resting heart rate, an immediately upon awakening standing still resting heart rate; a sometime after awakening standing still resting heart rate, a sometime after awakening in a recumbent position resting heart rate, a sometime after awakening in a sitting position resting heart rate, or a sometime after having completed a physical activity resting heart rate.

The reserve heart rate may be selected from one of the difference between the patient's maximal heart rate and a resting heart rate (RvHR), or the difference between the maximal heart rate and an activity heart rate (ARvHR).

The maximal heart rate, the reserve heart rate, or the resting heart rate may be selected based on at least one of an instantaneous heart rate value, a time of day, a state of the patient, a patient health status, a fitness level, environmental conditions, or at least one medication prescribed to the patient.

In some embodiments, the method may further comprise modifying the threshold value based on at least one of a time of day, a state of the patient, a patient health status, a fitness level, environmental conditions, or at least one medication prescribed to the patient. The threshold value may be modified while being based on an unchanged reference value.

Figure 4:
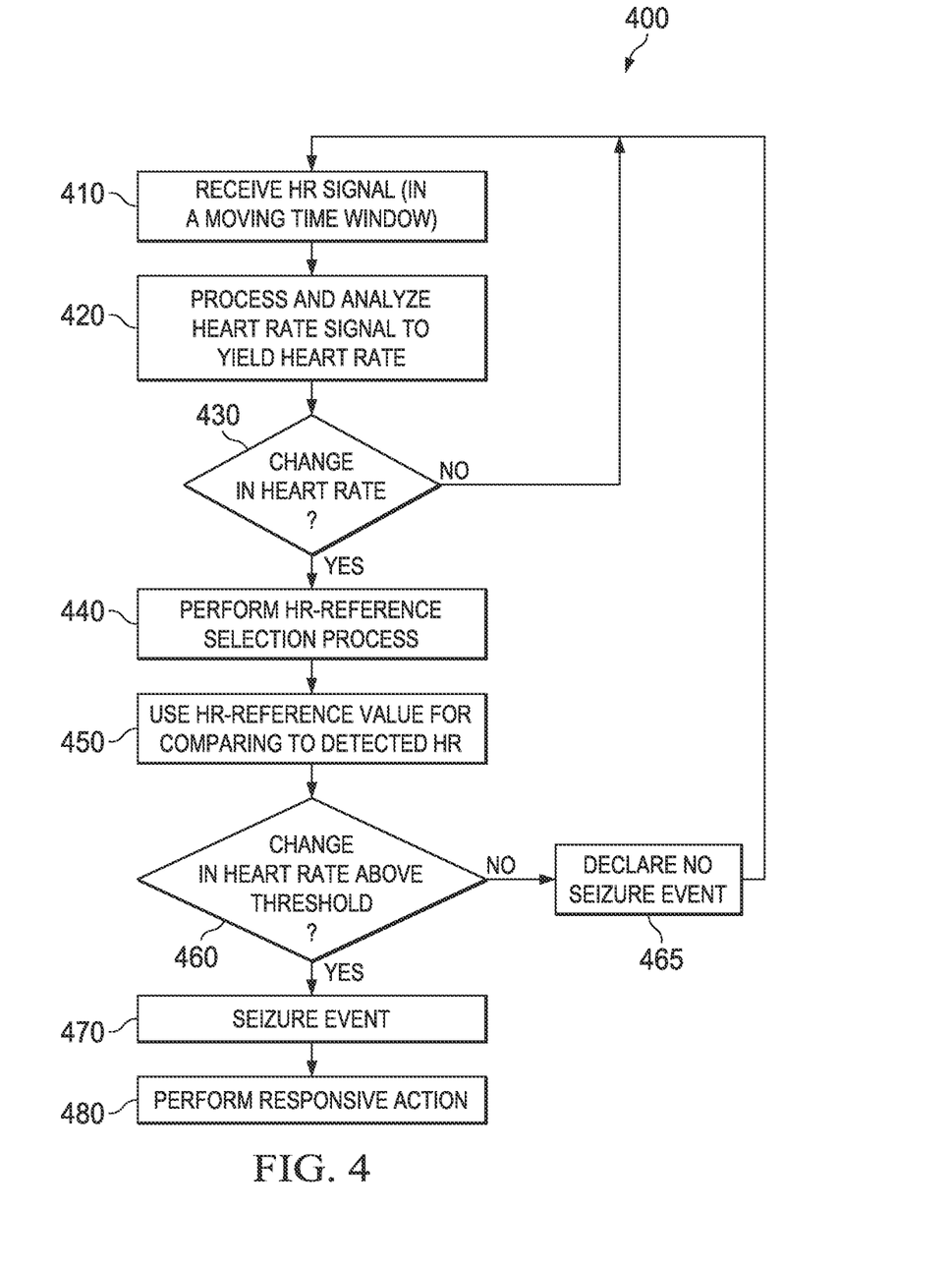
FIG. 4 shows a flowchart depiction of a method of detecting an epileptic seizure, according to some embodiments of the present disclosure.

Turning now to FIG. 4, a method 400 for performing a seizure detection, in accordance with an embodiment of the present disclosure, is illustrated. A heart rate signal may be acquired (at 410), for example in a moving time window. The heart rate signal may be processed and analyzed (at 420) to yield current measured heart rate (CMHR). In response (at 430) to a determination that said CMHR has changed or is above a threshold change, a HR-reference selection process may be performed (at 440), to select an MHR, a RvHR, a ARvHR or an RHR. A more detailed description of the HR-reference selection process is provided in FIGS. 5A and 5b and the accompanying description below.

Upon performing an HR-reference selection, the HR-reference value is compared and/or related to the CMHR (at 450). If the CMHR does not differ from the HR-reference by a threshold percentage (at 460), no seizure is declared (at 465). However, if the CMHR differs from the HR-reference by the threshold percentage (at 460), a seizure event is declared (at 470). Further, a responsive action may be taken (at 480), which may include issuing a warning, delivering a therapy, determining a seizure severity, or logging at least one of a data and time of the seizure, its severity, the type of therapy or its effect.

Figure 5A:
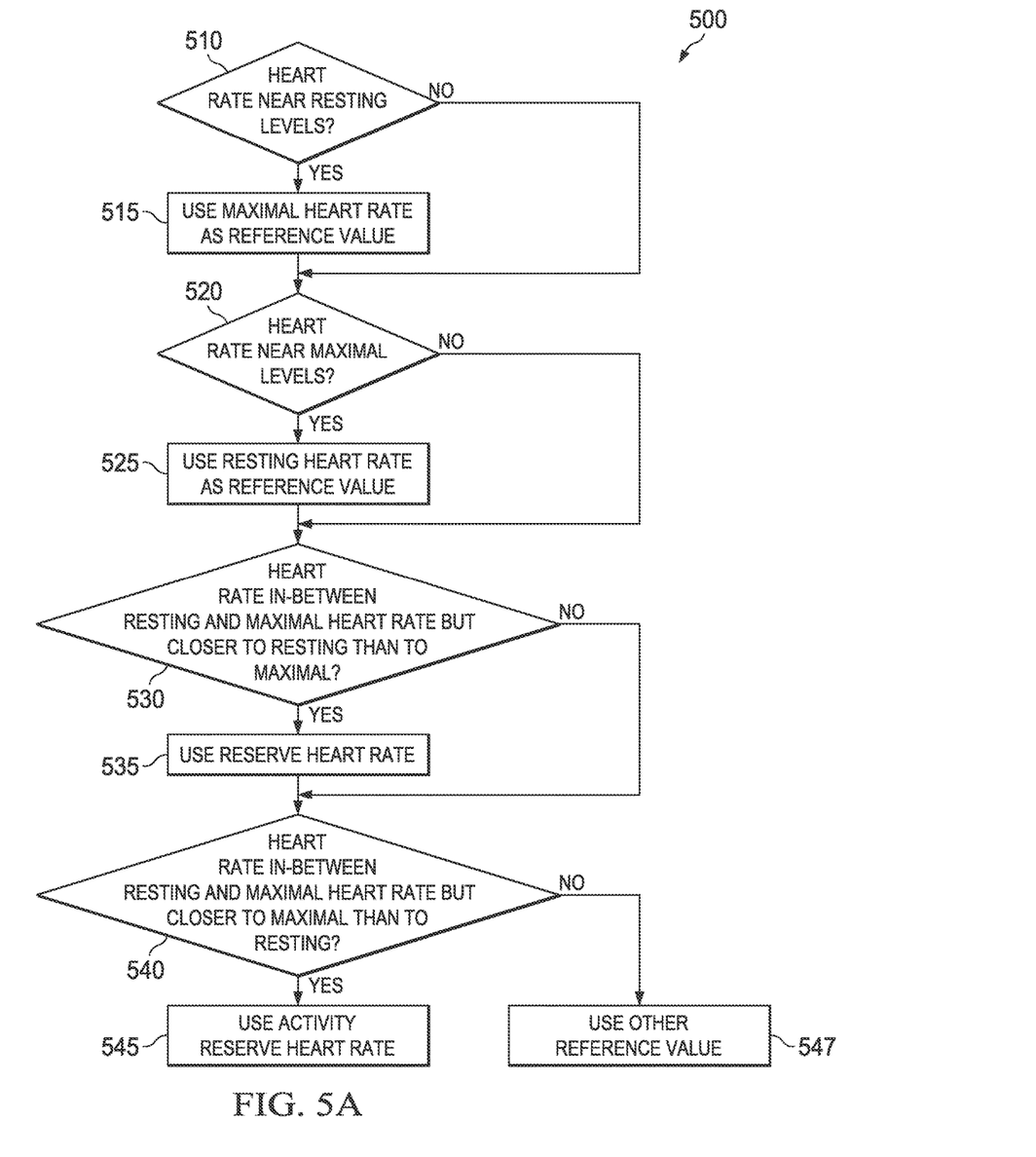
FIG. 5A shows a flowchart for selection of reference heart rates for detection of epileptic seizure, according to some embodiments of the present disclosure.
Figure 5B:
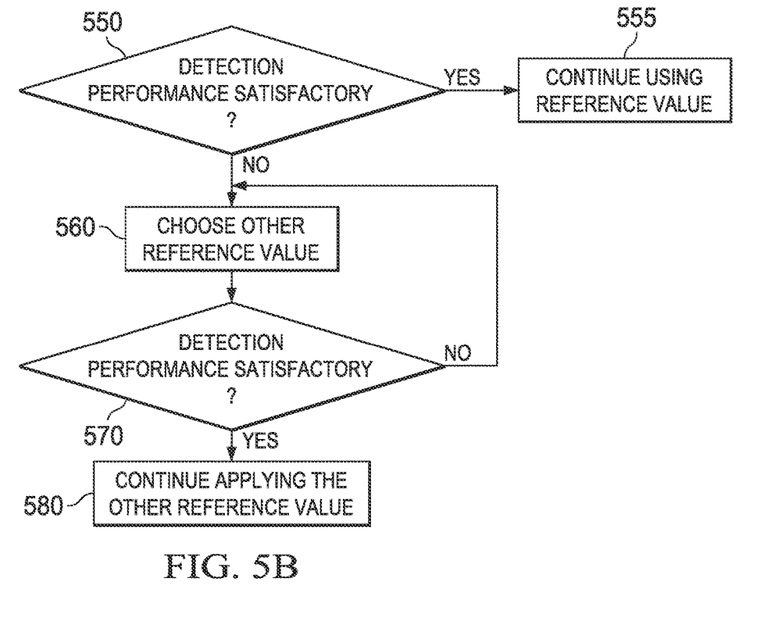
FIG. 5B shows a flowchart for selection "other reference values" (different from those shown in FIG. 5A) when detection performance using said FIG. 5A values are not satisfactory.

FIG. 5A and FIG. 5B depict a process of selecting the HR-reference. Examples of this HR-reference may include the MHR, RvHR, ARvHR or an RHR. A patient's heart rate may be determined using any appropriate technique and apparatus described above, included in a patent application incorporated herein by reference, or known to the person of ordinary skill in the art.

Alternatively or in addition to RHR, MHR, AHR, RvHR, and ARvHR, in one embodiment, other reference values may be derived from two or more of these values in any permutations and/or mathematical transformation (e.g., average value, ratios, etc. . . . ). Which HR-reference value(s) are to be selected may depend upon the current measured heart rate (CMHR) and its relative position related to either a minimal heart rate (e.g., RHR) or a maximum heart rate value (e.g., MHR). For example, the range of possible CMHR values spans between RHR and MHR. Inside this range is a mean, a median, or some other measure of central tendency. For a CMHR value between RHR and the measure of central tendency, the RHR may be selected as an initial HR-reference value upon which the permutation or other transformation may be based. For a CMHR value between the measure of central tendency and MHR, the MHR may be selected as the HR-reference value upon which the permutation or other transformation may be based.

This approach may reduce the search space and facilitate decision making in a computational cost effective way.

FIG. 5A depicts a flowchart representation of one method of selecting the HR-reference. If the patient's CMHR is determined to be at or near a resting level (at 510), then the patient's maximal heart rate may be used as the reference value (at 515). However, if the patient's heart rate is not near a resting level, then the method may comprise determining if the patient's CMHR is near the maximal level (at 520).

If the patient's CMHR is determined to be near the maximal level (at 520), then a resting heart rate (RHR) of the patient may be used as the reference value (at 525).

If the patient's heart rate is not near the maximal level, then the method may comprise determining if the patient's heart rate is between the mean or median value and the resting level (at 530). If the patient's CMHR falls within this range, then the patient's reserve heart rate (RvHR) may be used as the reference value (at 535).

If the patient's heart rate falls within the range of values between the mean or median and the maximal value (at 540), the patient's activity reserve heart rate (ARvHR) may be used as the reference value (at 545). If not, another reference value may be used (at 547).

As should be apparent to the person of ordinary skill in the art, in other embodiments, the HR reference may be selected from any one or more of MHR, RHR, RvHR, AHR, or ARvHR, and the candidate reference values may be examined in any order, i.e., not necessarily in an order that may be implied by FIG. 5A.

Turning to FIG. 5B, in some embodiments, once a HR-reference value is selected, a determination may be made whether the selected HR-reference value provides the desired sensitivity, specificity and speed of seizure detection. The determination as to whether the HR-reference performed to the desired levels may be based upon manual observation, secondary analysis, etc. If the determination were made that the selected HR reference is satisfactory, the patient's heart rate may be measured and compared to identified threshold values. However, if the determination were that the system response is unsatisfactory, other reference values can be identified and used. The quality of the performance (e.g, satisfactory, unsatisfactory) may be based on the number of false positive and/or false negative detections, and/or the speed of detection, for a reference value. Alternatively or in addition, in some embodiments, the positive predictive value may be used to assess the performance. False positive and false negative detections may be determined through validation/invalidation of a detection, or identification of a missed detection, using at least one different feature of the same body signal, at least one feature of a different body signal, visual expert or expert system analysis of the time series of the same or different body signal (on- or off-line), or two or more thereof.

FIG. 5B further elaborates on the end steps. At step 550, a determination is made whether or not detection performance is satisfactory. If the detection is satisfactory, then the process of FIG. 5A is repeated (at 555). However, if the determination is made that detection performance is unsatisfactory, a different reference value is selected (at 560). Once this different reference value is selected, another determination is made as to whether or not detection performance is satisfactory (at 570). If the detection performance is unsatisfactory, then the process repeats step 560. If the detection is satisfactory, then the detection algorithm continues to utilize the identified reference value (at 580).

By way of example, the process of adjusting automated seizure detections may be performed based on utilization of a percentage change in at least one of the: 1. maximal heart rate (MHR); 2. resting heart rate (RHR); 3. reserve heart rate (RvHR); or, 4. Activity reserve heart rate (ARvHR).

Taking the heart rate values of Example 1 above: MHR: 180 bpm; RHR: 60 bpm; RvHR: 120 bpm; PMHR: 140 bpm (indicating exercise); ARvHR: 40 bpm; Current Measured heart rate (CMHR): 155 bpm. The choice of reference value may be made based on the prevailing patient conditions, safety risks, or circumstances. For example, if a patient has partial seizures with secondary generalization (invariably associated with falls to the ground) that are abated if therapy is delivered within 5 sec of electrographic onset (while the patient is still aware and responsive and the patient is running), sensitivity and speed of detection must be maximized to minimize the probability of serious injuries should the patient have a seizure. In this case, an ARvHR (40 bpm) may be chosen as a reference to compute a ratio (140/40=3.5) that serves as a detection threshold. Any ratio values above 3.5 (as it would be the case when HR increase to 155 bpm: 155/40=3.9) such as 3.6 will trigger an early detection and therapy delivery likely to abate the seizure, thus protecting the patient from injuries. On the other hand, if a patient with partial seizures with secondary generalization is lying in bed and the anti-seizure therapy is efficacious but associated with intolerable side effects, specificity, not sensitivity or speed of detection, is paramount. In this case, the RvHR may be chosen to compute a ratio or to calculate a percentage or non-percentage increase in heart rate before a detection and other actions are taken in response to the seizure.

In a different case of Example 1, a detection may be issued if and when the current measured heart rate (CMHR) is one of: 22.2% of the MHR above the previously measured heart rate PMHR value; 33.3% of the RvHR above the PMHR value, or 66.7% of the RHR above the PMHR value. This is a form of detection "normalization" as the increase in bpm required to issue a detection in each alternative is the same (+40 bpm).

In one embodiment, the choice of heart rate reference value for a given patient in a given condition, state, safety risk, efficacy and side effects of a therapy, may be made based on the best trade-off between false negative and positive detections using for example receiver operating curves or some other optimization method.

The method depicted in FIGS. 5A and 5B may allow the detection of an epileptic event with improved sensitivity relative to prior methods. The sequence in which identified HR reference values are identified may be performed in various sequential or non-sequential orders.

The methods depicted in FIGS. 4-5B and/or described above may be governed by instructions that are stored in a non-transitory computer readable storage medium and that are executed by, e.g., a processor 217 of the medical device 200. Each of the operations shown in FIGS. 4-5B and/or described above may correspond to instructions stored in a non-transitory computer memory or computer readable storage medium. In various embodiments, the non-transitory computer readable storage medium includes a magnetic or optical disk storage device, solid state storage devices such as flash memory, or other non-volatile memory device or devices. The computer readable instructions stored on the non-transitory computer readable storage medium may be in source code, assembly language code, object code, or other instruction format that is interpreted and/or executable by one or more processors.

In some embodiments, the present disclosure may provide the following numbered paragraph(s):

A non-transitory computer readable program storage unit encoded with instructions that, when executed by a computer, perform a method for detecting a seizure, comprising: receiving a current measured heart rate (CMHR) of a patient; receiving at least one heart rate reference (HR-reference) selected from said patient's maximal heart rate, a reserve heart rate, an activity heart rate, or a resting heart rate; and detecting a seizure based on said CMHR and said HR-reference.

What is claimed:

1. A non-transitory computer readable program storage unit encoded with instructions that, when executed by a medical system, perform a method for detecting a seizure, comprising:

receiving via one or more processors of the medical system a heart rate of a patient;

calculating via the one or more processors of the medical system a change in the heart rate;

selecting via the one or more processors of the medical system, in response to a calculated change in the heart rate, at least one of a maximal heart rate, a reserve heart rate, an activity heart rate, and a resting heart rate;

detecting via the one or more processors of the medical system the seizure based on the change in the heart rate reaching a threshold value in reference to the selected at least one of the maximal heart rate, the reserve heart rate, the activity heart rate, and the resting heart rate; and initiating via the one or more processors a responsive action where the responsive action is a delivering of a therapy, in response to the detection.

2. The non-transitory computer readable program storage unit of claim 1, wherein the seizure is an epileptic or a non-epileptic seizure.

3. The non-transitory computer readable program storage unit of claim 1, wherein the resting heart rate is selected from at least one of a non-REM sleep heart rate (RSRsn-rem), a REM sleep heart rate (RSRsrem), an immediately upon awakening in a recumbent position resting heart rate, an immediately upon awakening in a sitting position resting heart rate, an immediately upon awakening standing still resting heart rate, a sometime after awakening standing still resting heart rate, a sometime after awakening in a recumbent position resting heart rate, a sometime after awakening in a sitting position resting heart rate, a heart rate while performing a physical activity, a resting heart rate after having completed a physical activity, a resting heart rate awake (RSRw), a heart rate associated with a cognitive activity, a heart rate associated with an emotional activity, and a resting heart rate asleep (RSRs).

4. The non-transitory computer readable program storage unit of claim 1, wherein the reserve heart rate is one of a first difference between the maximal heart rate and the resting heart rate, and a second difference between the maximal heart rate and the activity heart rate.

5. The non-transitory computer readable program storage unit of claim 1, wherein the selecting at least one of the maximal heart rate, the reserve heart rate, the activity heart rate, or the resting heart rate is based on at least one of an instantaneous heart rate value, a time of day, a state of the patient, an activity level of the patient, a patient health status, a patient fitness level, at least one environmental condition, and at least one medication prescribed to the patient.

6. The non-transitory computer readable program storage unit of claim 1, wherein the method further comprises modifying the threshold value based on at least one of a time of day, a state of the patient, a patient health status, a patient fitness level, an activity level of the patient, at least one environmental condition, and at least one medication prescribed to the patient.

7. The non-transitory computer readable program storage unit of claim 1, wherein the at least one responsive action is further selected from determining a seizure severity and logging at least one of: a date and time of occurrence of the seizure; the seizure severity; a type of therapy; and an effect of the therapy, in response to the detection.

8. The non-transitory computer readable program storage unit of claim 1, wherein the responsive action further includes issuing a warning.

* * * * *